(12) United States Patent
Cinquin et al.

(10) Patent No.: US 7,635,369 B2
(45) Date of Patent: Dec. 22, 2009

(54) KNEE DISTRACTOR

(75) Inventors: Philippe Cinquin, St Nazaire les Eymes (FR); Christophe Marmignon, Corenc (FR); Stéphane Lavallee, Saint Martin d'Uriage (FR)

(73) Assignee: Preception Raisonnement Action En Medecine, La Tronche (FR)

( * ) Notice: Subject to any disclaimer, the term of this patent is extended or adjusted under 35 U.S.C. 154(b) by 0 days.

(21) Appl. No.: 10/546,937

(22) PCT Filed: Feb. 27, 2004

(86) PCT No.: PCT/FR2004/050089

§ 371 (c)(1),
(2), (4) Date: Dec. 19, 2005

(87) PCT Pub. No.: WO2004/078047

PCT Pub. Date: Sep. 16, 2004

(65) Prior Publication Data

US 2006/0149277 A1 Jul. 6, 2006

(30) Foreign Application Priority Data

Feb. 27, 2003 (FR) ................................. 03 02413

(51) Int. Cl.
*A61B 17/56* (2006.01)
(52) U.S. Cl. ......................................................... 606/90
(58) Field of Classification Search .................. 606/90, 606/102, 105, 61, 88; 623/17.15, 20.14, 623/20
See application file for complete search history.

(56) References Cited

FOREIGN PATENT DOCUMENTS

| WO | WO 95/20362 | 8/1995 |
|---|---|---|
| WO | WO 99/59669 | 11/1999 |
| WO | WO 02/102254 A2 | 12/2002 |
| WO | WO 03/003951 A1 | 1/2003 |

*Primary Examiner*—Eduardo C Robert
*Assistant Examiner*—David Comstock
(74) *Attorney, Agent, or Firm*—Leason Ellis LLP

(57) ABSTRACT

A medical instrument includes a lower plate, at least one upper plate opposite the lower plate, a spacer means which is disposed between the upper plate and the lower plate. The spacer means is used to permanently hold the upper plate in a substantially parallel position in relation to the lower plate and to move the upper plate away from the lower plate. The spacer means is fully contained between the upper and the lower plate. The minimal spacing between the outer surfaces of the upper plate and the lower plate is less than ten (10) millimeters. A flexible control means is connected to the spacing means.

17 Claims, 1 Drawing Sheet

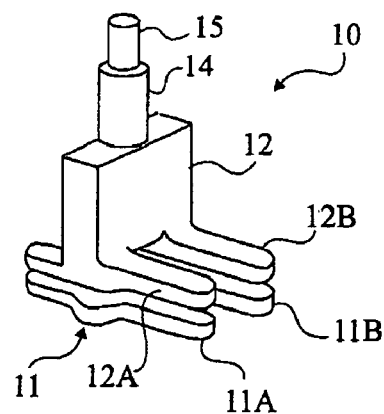
Fig 1 (PRIOR ART)
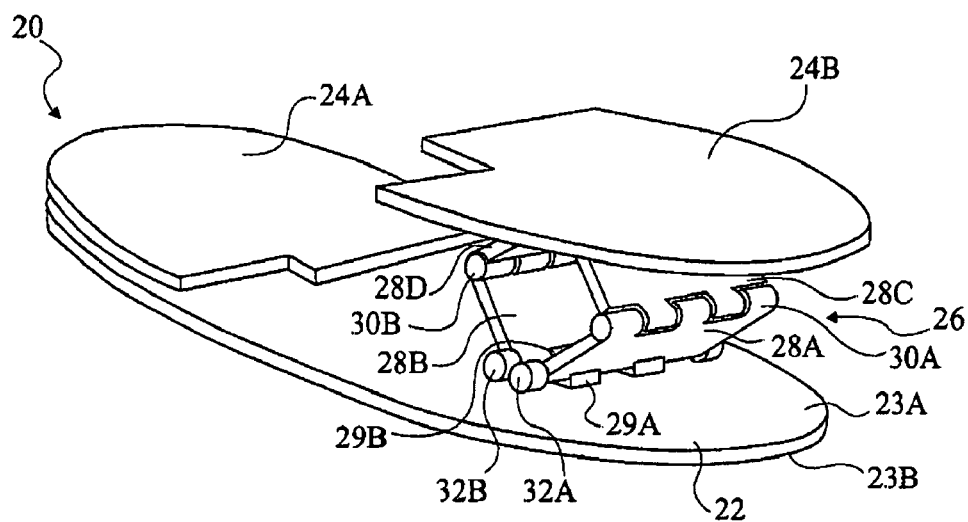
Fig 2
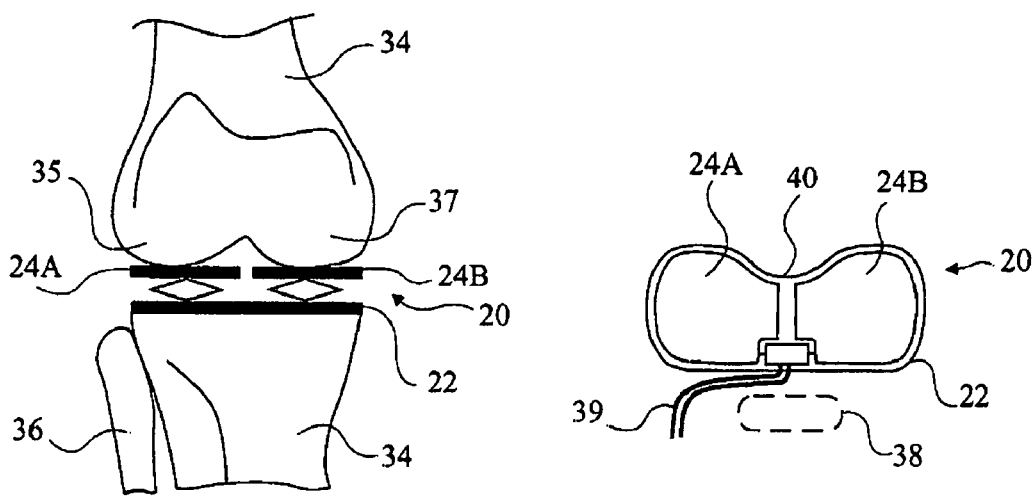
Fig 3
Fig 4

KNEE DISTRACTOR

CLAIM FOR PRIORITY

This application claims the benefit of French Application No. 03/02413, filed Feb. 27, 2003 and Int'l. Application No. PCT/FR2004/050089, filed Feb. 27, 2004 and is incorporated herein by reference.

FIELD OF THE INVENTION

The present invention relates to a knee distractor used in a knee prosthesis implantation operation.

BACKGROUND OF THE INVENTION

In an implantation operation, the surgeon must select the best-adapted prosthesis so that the patient recovers the greatest possible mobility. The prosthesis selection is partly determined by the state of the capsuloligamentary system of the knee. To obtain an optimal force distribution on the prosthesis, said prosthesis must be implanted in perfect alignment with the leg in extension and the joint space, that is, the region separating the femur from the tibia after the bone cuts have been performed, must have a height, corresponding to the shortest distance separating the femur from the tibia, identical in extension and for a 90° flexion of the leg. The equality in the joint space heights ensures an acceptable force distribution in the ligaments during flexion of the leg.

Further, given the knee deterioration, certain ligaments may have retracted with respect to a normal state. The surgeon must thus firstly estimate the behavior of the ligamentary system before implantation of the prosthesis. In particular, the surgeon may have to "relax" certain ligaments before implantation, that is, incise ligaments to enable them to reach a greater length.

To evaluate the height of the joint space and the state of the ligamentary system, the surgeon uses a medical instrument called a distractor which enables spacing the bone portions of the knee joint to measure the height of the joint space while placing the ligamentary system under tension.

FIG. 1 schematically shows an example of a conventional distractor 10. Distractor 10 comprises a base 11 from which two lower arms 11A, 11B intended to rest on the cut end of the tibia extend. Distractor 10 comprises a body 12 capable of sliding with respect to base 11 along a direction substantially perpendicular to the median plane of lower arms 11A, 11B. Body 12 comprises two upper arms 12A, 12B substantially parallel to lower arms 11A, 11B. Each upper arm 12A, 12B is intended to contact a condyle of the femur. Adjustment means 14, comprising an adjustment screw 15, are capable of sliding body 12 with respect to base 11 to adjust the position of upper arms 12A, 12B with respect to lower arms 11A, 11B.

To arrange distractor 10, the knee is maintained in extension and the surgeon performs an incision. The patella is everted, that is, it is displaced laterally with respect to its normal position and inverted, to free enough space to carry out the cutting of the upper end of the tibia and arrange distractor 10. Lower arms 11A, 11B and upper arms 12A, 12B are introduced into the joint space thus freed by the front of the joint, lower arms 11A, 11B being placed in contact with the cut end of the tibia. Body 12 of distractor 10 is displaced with respect to base 11 until upper arms 12A, 12B contact the condyles of the femur. The height of the joint space is then measured.

During the use of distractor 10, a portion of body 12 and of base 11 protrudes out of the joint space by the front of the knee joint. A disadvantage is that it is accordingly necessary to maintain the patella everted for as long as the distractor is used.

A measurement of the joint space and an indirect and qualitative appreciation of the forces exerted on the ligamentary system can thus be obtained only when the knee is in extension. To obtain an estimate of the joint space for another position of the leg, generally 90° of flexion, the surgeon must remove distractor 10 from the joint space, put the patella back in normal position, and finally bend the leg in the desired position. The surgeon relaxes the ligaments if necessary until the distractor, having a thickness which corresponds to the thickness of the joint space measured by the distractor for the leg in extension, is inserted back into the joint space.

Such a distractor thus does not enable following the variation of the joint space and of the forces exerted on the different elements of the joint according to the leg flexion. The selection of the prosthesis is then usually performed empirically from a single direct measurement of the geometry of the joint space. Further, in the case where a relaxing of the ligaments is necessary, said relaxing is performed by only taking into account the forces exerted on the ligamentary system for a given flexion, generally at 90°, which can appear to be unsatisfactory.

BRIEF SUMMARY OF THE INVENTION

The present invention aims at a distractor enabling spacing apart of bone portions of a knee joint prior to a prosthesis implantation to perform measurements of distances and forces characteristic of the joint at different flexion positions of the leg.

To achieve this object, the preset invention provides a medical instrument comprising a lower plate; at least one upper plate facing the lower plate; between the upper plate and the lower plate, spacing means for permanently maintaining the upper plate substantially parallel to the lower plate and for spacing apart the upper plate from the lower plate, said means being totally contained between the upper plate and the lower plate, the minimum interval between the external surfaces of the upper plate and of the lower plate being smaller than 10 millimeters; and flexible control means connected to the spacing means.

According to an embodiment of the invention, the medical instrument comprises two upper plates arranged side-by-side and facing the lower plate, each upper plate being associated with spacing means.

According to an embodiment of the invention, the medical instrument comprises means for measuring the distance between the upper plate and the lower plate.

According to an embodiment of the invention, the medical instrument comprises means for measuring the forces exerted on the upper plate.

According to an embodiment of the invention, the spacing means comprise a connection system formed of four links, two lower links connected to the lower plate by adjacent pivotal connections, and two upper links connected to the upper plate by adjacent pivotal connections, each lower link being connected to an upper link by a pivotal connection, the connection system further comprising means for maintaining the lower links substantially symmetrical with respect to the median plane perpendicular to the lower plate.

According to an embodiment of the invention, the spacing means comprise a cable actuation means and/or a fluid actuator connected to the lower plate and to the upper plate.

According to an embodiment of the invention, the external surface of the upper plate is planar.

According to an embodiment of the invention, the medical instrument is intended to space apart bone portions of a knee joint, the patella being in normal position, the lower plate being intended to be maintained at a cut end of the tibia, each upper plate being intended to be in contact with a condyle of the femur.

According to an embodiment of the invention, each spacing means is intended to be controlled for different leg flexion positions.

According to an embodiment of the invention, the lower plate and the upper plates comprise a recess on the side opposite to the side intended to be closer to the patella.

BREIF DESCRIPTION OF THE SEVERAL VIEWS OF THE DRAWINGS

The foregoing object, features, and advantages, as well as others, of the present invention will be discussed in detail in the following non-limiting description of specific embodiments in connection with the accompanying drawings, among which:

FIG. 1, previously described, schematically shows a perspective view of a conventional distractor;

FIG. 2 schematically shows a partial perspective view of an example of embodiment of a distractor according to the invention;

FIG. 3 schematically shows a front view of a distractor arranged at the level of a knee joint; and FIG. 4 schematically shows a top view of the distractor of FIG. 3.

DETAILED DESCRIPTION OF THE DRAWINGS

As shown in FIG. 2, distractor 20 according to the invention comprises a lower plate 22 having first and second substantially planar parallel surfaces 23A, 23B. Second surface 23B of lower plate 22 is intended to be maintained at the cut end of the tibia by anchoring means, not shown. Distractor 20 comprises two substantially planar upper plates 24A, 24B. Each upper plate 24A, 24B is connected to first surface 23A of lower plate 22 by a spacing system 26 (a single spacing system being visible in FIG. 2). Spacing system 26 enables displacement of the associated upper plate 24A, 24B with respect to lower plate 22 while permanently maintaining the median plane of upper plate 24A, 24B substantially parallel to first surface 23A of lower plate 22.

According to the present example of embodiment, spacing system 26 connecting an upper plate 24A, 24B to lower plate 22 comprises four links 28A to 28D arranged as a parallelepiped, two lower links 28A, 28B each connected to lower plate 22 by a lower pivotal connection 29A, 29B, and two upper links each connected to upper plate 24A, 24B by a pivotal connection (not visible in FIG. 2). Each lower link 28A, 28B is connected to an upper link 28C, 28D by an upper pivotal connection 30A, 30B. Lower pivotal connections 29A, 29B are adjacent and are associated with toothed wheels 32A, 32B to ensure a symmetrical clearance for the two lower links 28A, 28B with respect to a median plane perpendicular to lower plate 22. Similarly, the upper pivotal connections are adjacent and are associated with toothed wheels (not visible in FIG. 2) to ensure a symmetrical clearance for the two upper links 28C, 28D with respect to a median plane perpendicular to upper plate 24A, 24B. The structure of spacing system 26 is such that it is totally contained between upper plate 24A, 24B and lower plate 22.

As an example, upper plate 24A, shown to the left in FIG. 2, is in the position closest to lower plate 22. Upper plate 24B, shown to the right in FIG. 2, is in a position at a distance from lower plate 22 intermediary between the minimum distance and the maximum distance that can be reached. As an example, when both upper plates 24A, 24B are at a maximum distance from lower plate 22, the total thickness of distractor 20 according to the invention is approximately 20 millimeters, and when both upper plates 24A, 24B are at a minimum distance from lower plate 22, the total thickness of distractor 20 according to the invention is substantially smaller than 10 millimeters, and advantageously smaller than 5 millimeters.

Spacing system 26 also comprises, for each upper plate 24A, 24B, actuation means (not shown) capable of spacing apart upper plate 24A, 24B from lower plate 22. The actuation means associated with upper plates 24A, 24B can be actuated independently from each other to move upper plates 24A, 24B with respect to lower plate 22 independently from each other. According to an example of embodiment, the actuation means is a cable system. According to another example of embodiment, the actuation means comprises a fluid actuator, for example, an air piston, placed between the associated upper plate 24A, 24B and lower plate 22. The injection of a fluid, for example, compressed air, at the actuator level, ensures the separation of upper plate 24A, 24B from lower plate 22.

A distance sensor (not shown), arranged at the level of each upper plate 24A, 24B, is capable of measuring the distance separating upper plate 24A, 24B from lower plate 22. It is for example a Hall-effect sensor associated with a permanent magnet arranged at the level of lower plate 22. An force sensor (not shown), also arranged at the level of each upper plate 24A, 24B, is capable of measuring the forces exerted on upper plate 24A, 24B by spacing system 26. The distance and force sensors are, for example, directly integrated to the plates or are placed thereon.

FIG. 3 schematically shows distractor 20 according to the invention arranged in the joint space of the knee between tibia 34 and femur 35, once the tibial cutting has been performed. As an illustration, fibula 36 is also shown. As shown, lower plate 22 of distractor 20 is attached to the cut end of tibia 34 and upper plates 24A, 24B of lower plate 22 are in contact with condyles 37A, 37B of femur 35. Given the different shapes of condyles 37A, 37B, upper plates 24A, 24B are generally not spaced apart by a same distance from lower plate 22.

FIG. 4 shows a top view of distractor 20 of FIG. 3. The location of patella 38 has been shown in dotted lines. Cables and/or ducts 39 connect distractor 20 to a processing and control unit. Cables or ducts 39 transmit to the processing and control unit the data provided by the force or distance sensors and provide distractor 20 with the control of spacing systems 26. As an example, when spacing system 26 comprises a fluid actuator, a duct 39 is a fluid supply duct. Distractor 20 according to the invention is such that no element protrudes from the region located between upper plates 24A, 24B and lower plate 22 whatever the positions of upper plates 24A, 24B, except for cables and ducts 39. Distractor 20 according to the invention thus takes up a minimum space. Further, cables and ducts 39 are sufficiently flexible to be placed tightly along distractor 20. Distractor 20 according to the invention can thus be used while maintaining patella 38 in its normal position.

Further, lower plate 22 and upper plates 24A, 24B comprise a recess 40 on the side opposite to patella 38 to avoid disturbing the passing of the veins, arteries, nerves, ligaments, etc. in this part of the knee joint.

Distractor 20 according to the present invention is arranged at the level of the knee joint as follows.

An incision enabling access to the joint is performed. Patella 38 is then everted and the tibial cutting is performed. This frees the joint space between the cut end of tibia 34 and condyles 37A, 37B of femur 35 which has a height generally ranging between 5 and 10 millimeters. In the tibial cutting, the elements which will be replaced with the prosthesis are also suppressed, that is, the meniscus and, according to their state, certain ligaments, for example, the anterior and posterior cruciate ligaments. Distractor 20 according to the present invention is then inserted into the space thus freed. The inserting of distractor 20 according to the invention is eased by the fact that each upper plate 24A, 24B is in the position closest to lower plate 22. Distractor 20 thus has a small total thickness. Lower plate 22 of distractor 20 is attached to the cut end of tibia 34. Patella 38 is then put back in normal position. Upper plates 24A, 24B are then spaced apart from lower plate 22 via spacing system 26 until they are in contact with condyles 37A, 37B of femur 35. All the elements of the joint are then more or less placed under tension.

There are two possible ways for placing under tension. First, it is possible to impose the values of the forces applied at the level of upper plates 24A, 24B, that is, generally applied to the ligamentary system, by means of the force sensors. The distance separating each upper plate 24A, 24B from lower plate 22 is then measured via the distance sensor. Second, it is possible to impose the distances separating upper plates 24A, 24B from lower plate 22. The forces which are then undergone by upper plates 24A, 24B and which are then added to the forces generally exerted on the ligamentary system are then measured. Upper plates 24A, 24B can be actuated independently from each other. Distances separating upper plates 24A, 24B from lower plate 22 which are different for the two upper plates can thus be imposed. Similarly, forces applied at the level of upper plates 24A, 24B that are different for the two upper plates can be imposed.

The force and distance measurements are performed for different leg flexion positions. The two modes for placing the joint under tension especially enable controlling a measurement by alternately imposing the distance or the force. The different measurements obtained for different leg flexion positions enable the surgeon to appreciate the variation of the joint space and of the forces exerted on the ligamentary system for the entire leg flexion movement and thus help the surgeon in its selection of the most adapted prosthesis. Further, the distractor according to the present invention enables the surgeon to perform, at one or at different leg flexion positions, a ligamentary relaxing while controlling the effect of the relaxing by means of the information provided by the distractor.

The distractor according to the invention has a compact form since the spacing systems are totally contained between the upper plates and the lower plate. Further, the cables and ducts connected to the distractor are flexible to be easily moved and not disturb the motions of bone portions of the knee joint. An advantage of the present invention is to be able to use the distractor while maintaining the patella of the knee joint in normal position. The distractor can thus be used for different leg flexion positions.

Further, the distractor according to the present invention enables taking into account the patellofemoral space on determination of an ideal location for the implantation of the tibial prosthesis since the tensing measurements are performed when the patella is in place. Measurements can thus be performed in parallel to determine the patella displacement and measure its shape to implant a patellar prosthesis having the same trajectory as the patella.

According to a variation of the invention, the distractor comprises no distance sensors. The distance measurement between the upper plates and the lower plate, if desired, can be deduced from the positions of the tibia and of the femur. Indeed, in certain surgical operations, the positions of the femur and of the tibia are determined separately, for example, via rigid bodies attached to the femur and to the tibia, especially for the determination of cutting planes.

The present invention has been described in the context of a distractor comprising two upper plates arranged side-by-side and facing the lower plate and intended to each contact a condyle of the femur. It should be clear that the distractor may comprise but a single upper plate arranged opposite to the lower plate. Such a distractor is adapted to the forming of a prosthesis of unicompartimental type. It may for example be a knee prosthesis in which a portion only of the end of the tibia is cut. The lower plate is then intended to be attached at the level of the cut portion of the tibia and the single upper plate is intended to contact the condyle of the femur opposite to the cut portion of the tibia.

Of course, the present invention is likely to have various alterations and modifications which will readily occur to those skilled in the art. In particular, the upper plates may be maintained substantially parallel to the lower plate by a cable mechanism.

The invention claimed is:

1. A medical instrument comprising:
a lower rigid plate;
at least one upper rigid plate facing the lower plate;
between the upper rigid plate and the lower rigid plate, spacing means for spacing apart the upper rigid plate from the lower rigid plate, wherein said spacing means permanently maintains said upper rigid plate substantially parallel to said lower rigid plate and wherein said means is totally contained between the upper rigid plate and the lower rigid plate, the minimum interval between the external surfaces of the upper rigid plate and of the lower rigid plate being smaller than 10 millimeters; and
flexible control means connected to the spacing means.

2. The medical instrument of claim 1, comprising two upper rigid plates arranged side-by-side and facing the lower rigid plate, each upper rigid plate being associated with spacing means.

3. The medical instrument of claim 2, in which the lower rigid plate and the upper rigid plates comprise a recess on the side opposite to the side intended to be closer to the patella.

4. The medical instrument of claim 1, comprising means for measuring the distance between the upper rigid plate and the lower rigid plate.

5. The medical instrument of claim 1, comprising means for measuring the forces exerted on the upper rigid plate.

6. The medical instrument of claim 1, in which the spacing means comprise a connection system formed of a series of links connected to each other and to the lower rigid plate and to the upper rigid plate by pivotal connections.

7. The medical instrument of claim 1, in which the spacing means comprise a connection system formed of four links, two lower links connected to the lower rigid plate by adjacent pivotal connections, and two upper links connected to the upper rigid plate by adjacent pivotal connections, each lower link being connected to an upper link by a pivotal connection, the connection system further comprising means for maintaining the lower links substantially symmetrical with respect to the median plane perpendicular to the lower rigid plate.

8. The medical instrument of claim 1, in which the external surface of the upper rigid plate is planar.

9. The medical instrument of claim 1, in which the spacing means comprises a fluid actuator connected to the lower rigid plate and to the upper rigid plate.

10. A medical instrument comprising:
   a lower rigid plate;
   an upper rigid plate facing the lower rigid plate;
   an actuator that spaces apart the lower rigid plate from the upper rigid plate, the minimum interval between the external surfaces of the upper rigid plate and of the lower rigid plate being smaller than 10 millimeters;
   a linkage mechanism comprising a series of links connected to each other and to the lower rigid plate and to the upper rigid plate by pivotal connections, the linkage mechanism contained entirely between the upper rigid plate and the lower rigid plate, the linkage mechanism permanently maintaining the upper rigid plate substantially parallel to said lower rigid plate.

11. The medical instrument of claim 10, further comprising a flexible controller connected to the actuator.

12. The medical instrument of claim 11, wherein the actuator is responsive to the controller for changing the separation distance between the upper and lower rigid plates.

13. The medical instrument of claim 10, wherein the actuator comprises a fluid actuator.

14. The medical instrument of claim 10, further comprising:
   another upper rigid plate facing the lower rigid plate, and
   a linkage mechanism comprising a series of links connected to each other and to the lower rigid plate and to the another upper rigid plate by pivotal connections, the linkage mechanism contained entirely between the another upper rigid plate and the lower rigid plate, the linkage mechanism permanently maintaining the another upper rigid plate substantially parallel to the lower rigid plate, wherein the separation distance between the another upper rigid plate and the lower rigid plate is changed in response to actuation by an actuator, and whereby the linkage mechanism maintains the upper rigid plate substantially parallel to the lower rigid plate throughout the change in separation distance and including when a load is applied to an outer portion of the upper or lower rigid plate.

15. The medical instrument of claim 14, wherein the upper rigid plate and the another upper rigid plate are actuable independently from one another whereby the relative separation distances between the lower rigid plate and the upper rigid plate and another upper rigid plate are independent from each other.

16. The medical instrument of claim 10, wherein the linkage system is formed of four links, two lower links connected to the lower rigid plate by adjacent pivotal connections, and two upper links connected to the upper rigid plate by adjacent pivotal connections, each lower link being connected to an upper link by a pivotal connection, the linkage mechanism maintaining the lower links substantially symmetrical with respect to the median plane perpendicular to the lower rigid plate.

17. The medical instrument of claim 10, further comprising a distance sensor disposed on at least one of the lower and upper rigid plates and capable of measuring the separation distance there between.

* * * * *